US00PP29259P3

(12) United States Plant Patent
Van Swieten

(10) Patent No.: US PP29,259 P3
(45) Date of Patent: Apr. 24, 2018

(54) *PHALAENOPSIS* ORCHID PLANT NAMED 'PHALUFREL'

(50) Latin Name: ***Phalaenopsis* hybrid**
Varietal Denomination: PHALUFREL

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 7 days.

(21) Appl. No.: 15/330,172

(22) Filed: Aug. 18, 2016

(65) Prior Publication Data

US 2018/0054938 P1 Feb. 22, 2018

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

UPOV-PLUTO: Plant Variety Database, citation for 'PHALUFREL' retrieved from the Internet on Oct. 21, 2017 (1 page total).*
EU Community Plant Variety Rights Application No. 2016/0970, Application n°A201600659, filed Apr. 18, 2016, 8 pages.
EU Community Plant Variety Office Official Gazette, Mar. 2016, Jun. 15, 2016, cover page and pp. 35, 52.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALUFREL', particularly characterized by having purple flowers with unique eye-catching light purple edge, 1 to 2 peduncles, leaves that are obovate, and is propagated by meristem tissue culture, is disclosed.

3 Drawing Sheets

Genus and species: *Phalaenopsis* hybrid.
Variety denomination: 'PHALUFREL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALUFREL'.

The new *Phalaenopsis* plant is a product of a planned breeding program conducted by the inventor in Bleiswijk, The Netherlands. The objective of this breeding program was to create a new *Phalaenopsis* plant with purple flowers having unique, eye-catching light purple edges, suitable for potted plant production.

The new *Phalaenopsis* plant 'PHALUFREL' is a result of cross-pollination made by the inventor in August 2007 in Bleiswijk, The Netherlands of the proprietary female, or seed parent, *Phalaenopsis* hybrid '01-2114' (unpatented) with the proprietary male, or pollen parent, *Phalaenopsis* hybrid '01-2134' (unpatented).

The new *Phalaenopsis* was selected by the inventor as a single plant within the progeny of the stated cross-pollination in a controlled greenhouse in Bleiswijk, The Netherlands in August 2010. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALUFREL' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALUFREL' as a new and distinct variety of *Phalaenopsis* plant.

1) Purple flowers with unique, eye-catching light purple edge;
2) 1 to 2 peduncles; and
3) Shape of the leaf is obovate.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in July 2016. Colors in the photographs may differ from the color values cited in the detailed botanical description, which accurately describe the actual colors of the new variety.

DESCRIPTION OF THE NEW VARIETY

Figure 1:
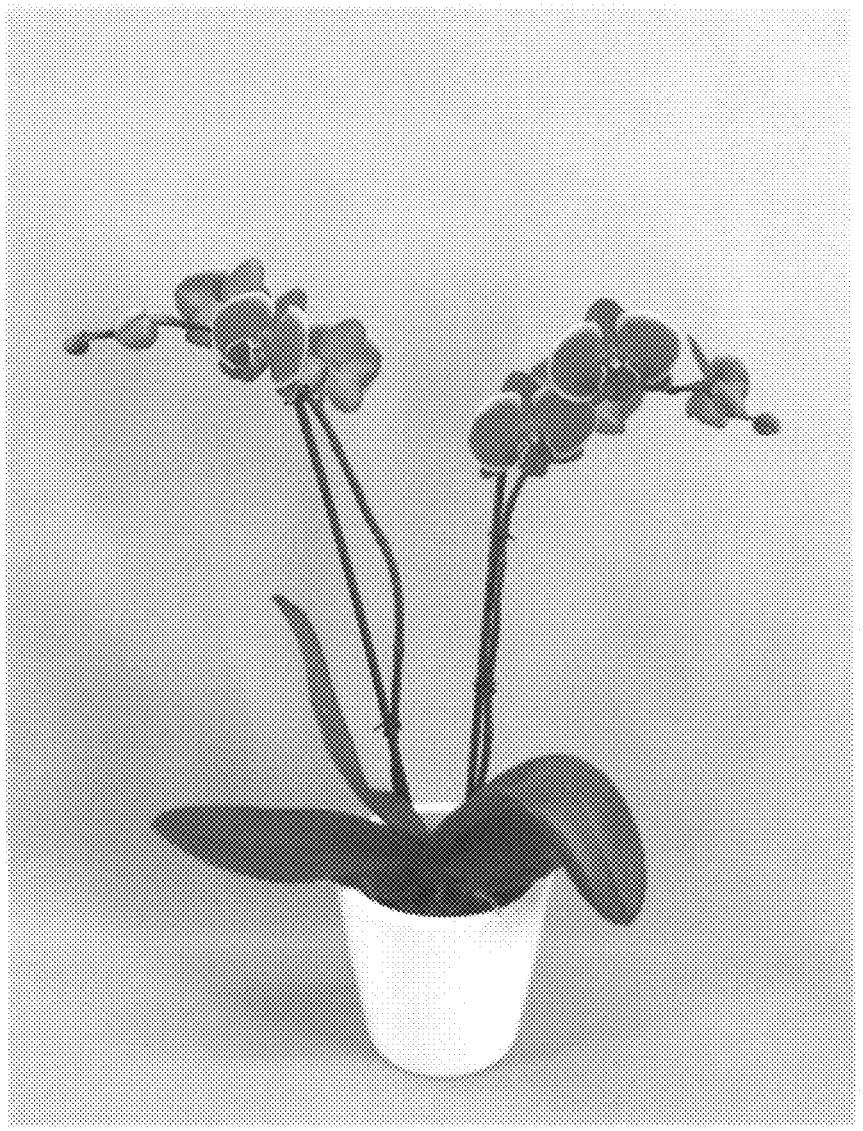
FIG. 1 shows the overall plant habit, including blooms, buds and foliage of 'PHALUFREL'.
Figure 2:
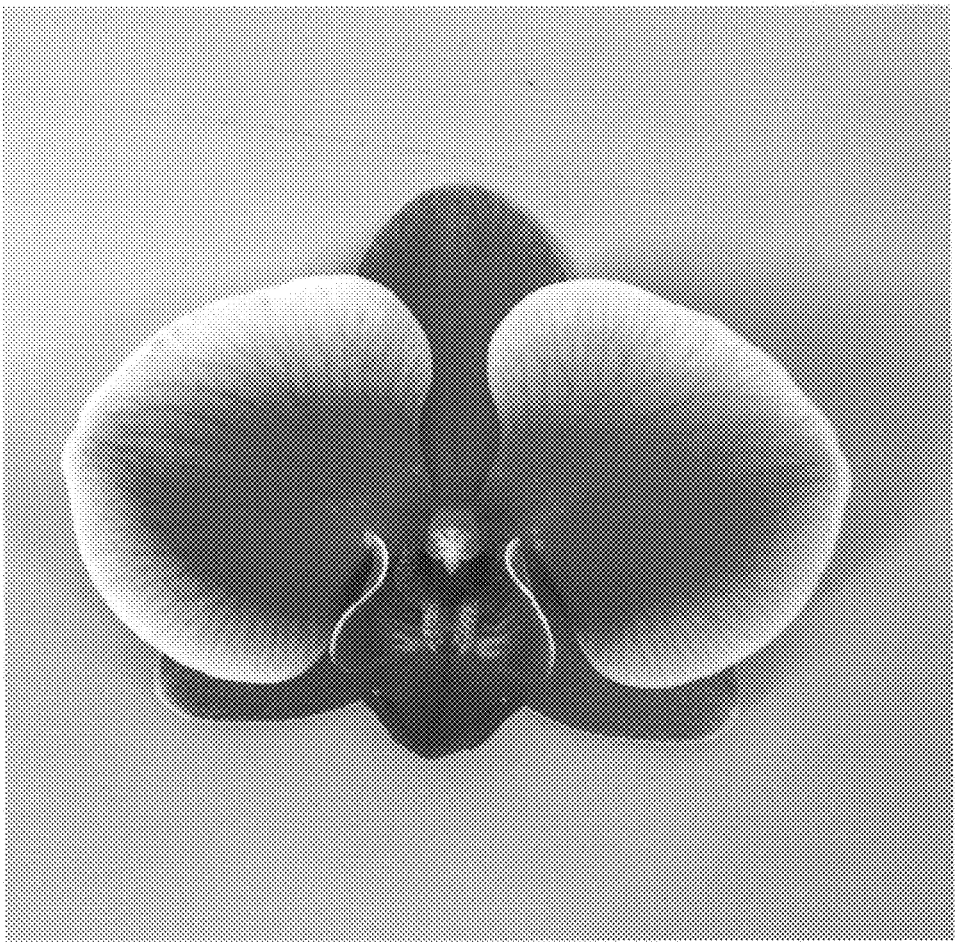
FIG. 2 shows a close-up of a flower of 'PHALUFREL'.
Figure 3:
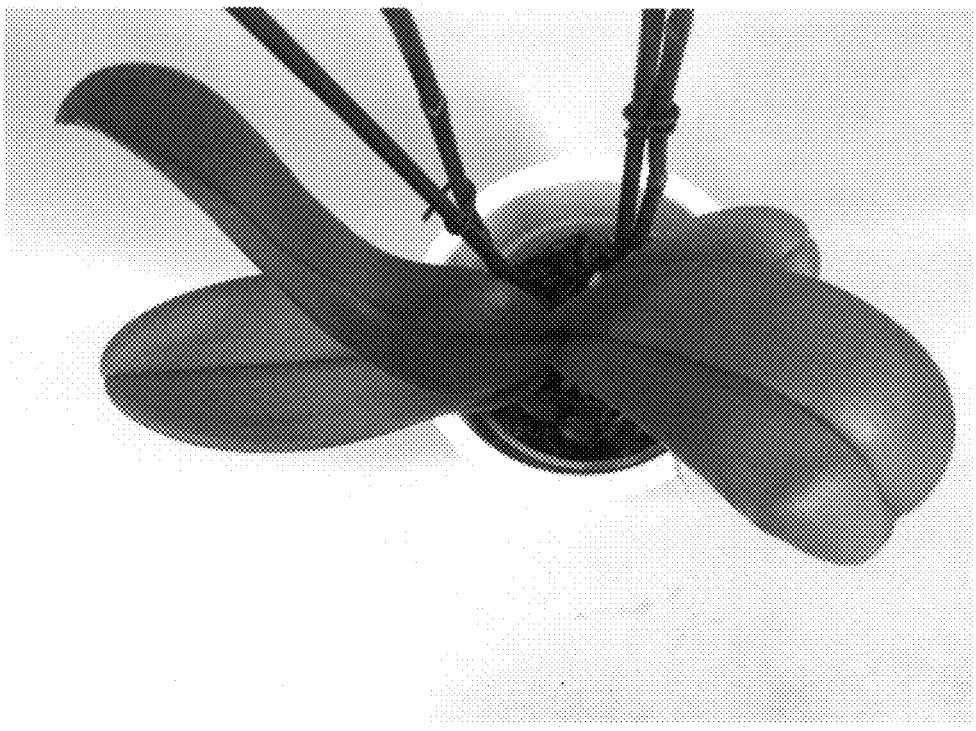
FIG. 3 shows a close-up of the leaves of 'PHALUFREL'.

The following detailed description sets forth the distinctive characteristics of 'PHALUFREL'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in July 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHALUFREL'.

Parentage:
- *Female parent*.—*Phalaenopsis* cultivar '01-2114' (unpatented).
- *Male parent*.—*Phalaenopsis* cultivar '01-2134' (unpatented).

Propagation:
- *Type*.—Meristem tissue culture.

Roots:
- *Root description*.—Greyed-green colored roots with slightly branching lateral roots having light purple colored root tips.

Plant:
- *Commercial crop time to flowering*.—Approximately 48 to 50 weeks from a rooted cutting to finish in a 12 cm pot.
- *Growth habit of peduncle*.—Standard, green leaves, panicle.
- *Height* (*from soil level to top of inflorescence*).—Approximately 44.0 cm to 54.0 cm.
- *Width* (*measured from leaf tips*).—About 33.0 cm to 37.0 cm.
- *Vigor*.—Strong.

Leaves:
- *Mature leaves*.—Quantity per plant: 5 to 7 leaves are produced before flowering. Length (fully expanded): 19.0 cm to 22.0 cm. Width: 8.0 cm to 9.0 cm. Shape: Obovate. Base shape: Moderately elongated. Apex: Rounded unequal. Leaf blade angle with the petiole (measured from the horizontal position): Between 25 degrees and 35 degrees. Leaf margin: Entire. Color: Upper surface: RHS 146A. Lower surface: RHS 146B, with purple edge (RHS 187A). Texture: Rough. Thickness: 2.3 mm to 2.6 mm. Venation: Pattern: Parallel. Color of the midvein: Upper surface: RHS 147A. Lower surface: RHS 146A.

Peduncle:
- *Quantity per plant*.—1 to 2.
- *Number of flowers per peduncle*.—8 to 12.
- *Length*.—44.0 cm to 55.0 cm.
- *Diameter*.—5.3 mm to 5.6 mm.
- *Strength*.—Strong.
- *Aspect*.—Upright to slightly pendant.
- *Texture*.—Smooth.
- *Color*.—Purple-brown (RHS 187A) with a touch of green (RHS 146B).
- *Internode length*.—3.5 mm to 4.5 mm.
- *Callosities*.—None.

Inflorescence description:
- *Appearance*.—Upright to slightly pendant, panicle inflorescence with bilaterally symmetrical flowers that open in succession beginning with the lowermost flower.
- *Inflorescence size*.—Height (from base to tip): 170.0 mm to 200.0 mm.
- *Flowering time*.—First flowers can be expected 10 to 11 months after planting in a 12 cm (diameter) pot.
- *Flower*.—Height: 74.0 mm to 76.0 mm. Diameter: 88.0 mm to 90.0 mm. Depth of lip: 20.0 mm to 22.0 mm.
- *Flower longevity*.—On the plant: 9 to 13 weeks.
- *Fragrance*.—Absent.
- *Flower bud*.—Average size: Medium. Length: 18.0 mm to 20.0 mm. Width: 16.0 mm to 18.0 mm. Shape: Egg shaped. Color: Dark purple (RHS 187B) with a touch of green (RHS 146D).
- *Petals*.—Arrangement: Open/free. Shape: Semi-circular. Apex: Rounded asymmetric. Margin: Entire. Length (from base to tip): 38.0 mm to 40.0 mm. Width: 52.0 mm to 55.0 mm. Color (when fully opened): Upper surface: Basic color: Purple (RHS N78A). Over color: Light purple (RHS 76C). Lower surface: Basic color: Purple (RHS N78B). Over color: Light purple (RHS 76C).
- *Dorsal sepal*.—Shape: Elliptic. Apex: Obtuse symmetric. Margin: Entire. Length (from base to tip): 44.0 mm to 46.0 mm. Width: 31.0 mm to 33.0 mm. Color (when fully opened): Upper surface: Basic color: Purple (RHS N78A). Over color: Absent. Lower surface: Basic color: Purple (RHS N78C). Over color: Light purple in the middle (RHS N76C).
- *Lateral sepals*.—Shape: Ovate. Apex: Obtuse asymmetric. Margin: Entire. Length (from base to tip): 40.0 mm to 42.0 mm. Width: 28.0 mm to 30.0 mm. Color (when fully opened): Upper surface: Basic color: Purple (RHS N78A). Over color: Red-purple (RHS 71A). Lower surface: Basic color: Purple (RHS N78C.) Over color: Light purple (RHS 78C/D).
- *Labellum* (*lip*).—Whiskers: Present. Length of whiskers: 6.0 mm to 8.0 mm. Color of whiskers: Purple (RHS 187A) with white tips (RHS NN155C). Pubescence on the lip: Absent.
- *Lateral lobe*.—Shape: Spatulate. Margin: Slightly undulated. Length (from base to tip): 20.0 mm to 23.0 mm. Width: 15.0 mm to 17.0 mm. Color: Red-purple (RHS 59A and N78A) with white (RHS NN155C) and slight yellow edge (RHS 7A).
- *Apical lobe*.—Shape: Triangular. Margin: Entire. Length: 20.0 mm to 22.0 mm. Width: 21.0 mm to 23.0 mm. Color: Red-purple (RHS 59A).

*Callus*.—Average size: Medium to large. Height: 0.7 cm to 0.9 cm. Length: 0.6 cm to 0.8 cm. Width: 0.4 cm to 0.6 cm. Color: Yellow (RHS 10C) with spots (RHS 183C).

*Reproductive organs*.—Column: Length: 8.0 mm to 10.0 mm. Diameter: 5.4 mm to 5.5 mm. Color: Purple (RHS N78A). Pollinia: Quantity: 2. Diameter: 1.0 mm to 1.2 mm. Color: Orange (RHS 24A). Ovary (part of pedicel with small ribs towards the column): Length: 9.0 mm to 11.0 mm. Diameter: 2.4 mm to 2.6 mm. Pedicel: Length: 39.0 mm to 41.0 mm. Diameter: 3.0 mm to 3.2 mm. Color: Purple (RHS N77B); towards the flower light green (RHS 193A) and light purple (RHS N78D).

Disease, pest, and stress resistance: No specific resistance or susceptibility has been observed to pathogens and pests common to *Phalaenopsis*.

Fruit and seeds: Fruit and seed development has not been observed on plants of the new *Phalaenopsis* to date.

COMPARISON WITH PARENTAL AND COMMERCIAL VARIETIES

The female parent of 'PHALUFREL', *Phalaenopsis* cultivar '01-2114' (unpatented), is no longer in existence so a meaningful comparison cannot be made.

The male parent of 'PHALUFREL', *Phalaenopsis* cultivar '01-2134' (unpatented), is no longer in existence so a meaningful comparison cannot be made.

'PHALUFREL' is most similar to the commercial *Phalaenopsis* plants named 'PHALDANBO' (U.S. Plant Pat. No. 25,930) and '01-2165' (unpatented). 'PHALUFREL' differs from the commercial variety 'PHALDANBO' in that 'PHALUFREL' has sepals with light purple lower surfaces, flowers with a broad edge pattern, and a lateral lobe of the lip with an edge pattern, whereas 'PHALDANBO' has sepals with purple lower surfaces, flowers with an even pattern, and a lateral lobe of the lip with an even pattern. Additionally, 'PHALUFREL' has shorter whiskers than 'PHALDANBO'.

'PHALUFREL' differs from similar variety '01-2165' in that 'PHALUFREL' has flowers with a broad edge pattern and sepals with light purple (RHS N78C/D) lower surfaces, whereas '01-2165' has flowers with a small edge pattern and sepals with light purple (RHS 76C) lower surfaces with an edge (RHS N80C).

I claim:

1. A new and distinct variety of *Phalaenopsis* plant named 'PHALUFREL', substantially as described and illustrated herein.

* * * * *